United States Patent [19]

Vrckovnik et al.

[11] Patent Number: 5,378,787
[45] Date of Patent: Jan. 3, 1995

[54] FIBER REACTIVE AMINO DIMETHICONE COPOLYOLS

[75] Inventors: Rick Vrckovnik, North York, Canada; Anthony J. O'Lenick, Jr., Lilburn, Ga.

[73] Assignee: Siltech Corporation, Toronto, Canada

[21] Appl. No.: 210,934

[22] Filed: Mar. 21, 1994

[51] Int. Cl.⁶ .............................................. C08G 77/08
[52] U.S. Cl. ....................... 528/14; 528/33; 528/38
[58] Field of Search .............................. 528/38, 33, 14

[56] References Cited

U.S. PATENT DOCUMENTS

| | | |
|---|---|---|
| 3,511,699 | 5/1970 | Sterman . |
| 4,467,068 | 8/1984 | Maruyama et al. ................. 528/38 |
| 5,075,403 | 12/1991 | Kirk . |
| 5,300,611 | 4/1994 | Fujioka et al. ........................ 528/38 |

Primary Examiner—Melvyn I. Marquis

[57] ABSTRACT

The invention relates to a series of novel silicone reactive amino containing dimethicone copolyols. This class of compounds provides unique softening, durability and solubility properties when applied to fibers including textile fibers and hair and skin. The compounds of the present invention contain (a) an amino group, (b) an alkylene oxide containing portion, (c) a reactive group selected from the group consisting of silanol hydroxyl and optionally a alkoxy group. The compounds of the invention are self dispersing in water, by virtue of the alkylene oxide, softening to fiber, by virtue of the amino group and durable by virtue of the silanol and/or hydroxyl group. An additional critically important aspect of the molecule is the fact that it is water soluble or dispersible resulting in stable aqueous systems for delivery to the fiber.

14 Claims, No Drawings

FIBER REACTIVE AMINO DIMETHICONE COPOLYOLS

BACKGROUND OF THE INVENTION

FIELD OF THE INVENTION

The invention relates to a series of novel silicone reactive amino containing dimethicone copolyols. This class of compounds provides unique softening, durability and solubility properties when applied to fibers including textile fibers and hair and skin. The compounds of the present invention contain (a) an amino group, (b) an alkylene oxide containing portion, (c) a reactive group selected from the group consisting of silanol hydroxyl and alkoxy group and a (d) a highly branched three dimensional structure. The compounds of the invention are self dispersing in water, by virtue of the alkylene oxide, softening to fiber, by virtue of the amino group and durable by virtue of the silanol and/or hydroxyl group. An additional critically important aspect of the molecule is the fact that it is water soluble or dispersible resulting in stable aqueous systems for delivery to the fiber.

The compounds find application as textile and personal care softeners and can be mixed with water to form sheer stable solutions or microemulsions without the need for high energy sheer devices like homogenizers, and without the need for emulsifiers. These products are surfactant free, reactive amino silicones which have outstanding durability to fibers.

ARTS AND PRACTICES

Silicone compounds have been known to be active at the surface of cellulosic and synthetic fibers as well as paper. They are good nondurable lubricants and are very stable to oxidation, however, their high cost and lack of efficiency at low concentrations as well as low durability have made their acceptance in commercial products quite low.

In addition to their high cost, silicone compounds have little or no solubility in mineral oils, fatty triglycerides and other classical fatty quaternary compounds used for softening. This has resulted in the inability to prepare stable blends for use as a textile fiber treatment.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer.

Silicone oils and amino silicone are emulsified with surface active agents and in a subsequent step homogenized to produce semi-stable milky white liquids which deliver the oil from a micelle. The difficulty with such a system is the fact that the micelle is subject to many destabilizing affects including heat, freezing, mechanical sheer, addition of acids or bases or the addition of additional detergents or emulsifiers. This has limited the usefulness of the emulsions to systems which have very limited added ingredients. Even when such materials are used in emulsion form they are not durable to the fiber being treated. When the fiber being treated is going into a garment, the garment is washed many times over it's useful life. Standard silicone oils and amino silicone oils wash off and the lubrication and softness which are required for a useful garment life is lost. The compounds of the present invention overcome these shortcomings of the prior art.

U.S. Pat. No. 5,075,403 to Kirk is aimed at amino/-polyoxyalkylenated silicone compounds. These materials lack the three dimensional branched structure, the silanol hydroxyl group and are not functional in this invention.

None of these cited references adequately address the combination of softness, water dispersability, durability and softness. As will become clear from the disclosure, the exact structure and the exact type of functional group present on the molecule will determine the effectiveness of the durable, water soluble or dispersible softener chosen.

THE INVENTION

Object of the Invention

It is the object of the present invention to provide a series of novel silicone compounds which contain (a) an amino group, (b) an alkylene oxide containing portion, (c) a reactive group selected from the group consisting of silanol hydroxyl and alkoxy group and (d) a highly branched three dimensional structure which allows the molecule to provide efficient durable non-yellowing softening and lubrication properties to fibers while being water soluble or dispersible providing ease of formulation and use.

It is another objective of the current invention to provide a process for the treatment of fibers with the compounds of the present invention. The process comprises contacting the fiber or textile fabric with an effective softening amount of a durable softener of the present invention. The process is preferably carried out in aqueous solution at a concentration of softener of between 0.1 and 10.0%.

Still other objectives will become clear as the teachings of the invention are read.

SUMMARY OF THE INVENTION

The invention relates to a series of novel silicone reactive amino containing dimethicone copolyols. This class of compounds provides unique softening, durability and solubility properties when applied to fibers including textile fibers and hair and skin. The compounds of the present invention contain (a) an amino group, (b) an alkylene oxide containing portion, (c) a reactive group selected from the group consisting of silanol hydroxyl and alkoxy group. The compounds of the invention are self dispersing in water, by virtue of the alkylene oxide, softening to fiber, by virtue of the amino group and durable by virtue of the silanol and/or hydroxyl group. An additional critically important aspect of the molecule is the fact that it is water soluble or dispersible resulting in stable aqueous systems for delivery to the fiber.

As will become clear from the disclosure, the compounds of the present invention not only require all of the functional components a-c described above but need them in the correct ration and in the correct three dimensional structure to be effective.

The compounds of the invention are prepared by the sequential reaction of an amino trialkoxy silane and a silanol, followed by the reaction of that product with a dimethicone copolyol in the presence of alkaline catalyst. An example is as follows;

Reaction Sequence 1

Silanol Containing Silane Preparation

In this step a alkoxy silane is reacted with a silanol to produce a alkoxy silanol which is a key intermediate in the preparation of the compounds of the present invention. The reactants are:

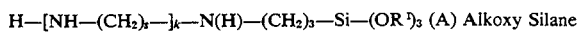
H—[NH—(CH₂)ₛ—]ₖ—N(H)—(CH₂)₃—Si—(OR¹)₃ (A) Alkoxy Silane k is an integer ranging from 0 to 3;
s is an integer ranging from 1 to 3;
R1 is methyl or ethyl;

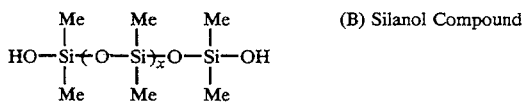

(B) Silanol Compound x is an integer from 10 to 2000;
Me is methyl.

The reaction results in a polymer but in the simplest case the reaction proceeds as follows;

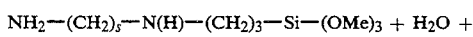
NH₂—(CH₂)ₛ—N(H)—(CH₂)₃—Si—(OMe)₃ + H₂O +

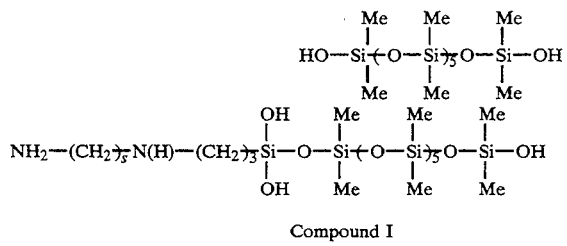

Compound I

Me is methyl;
s is an integer ranging from 1 to 3.

This material continues to condense to form the highly branched polymers. This is due to the condensation of the silanol hydroxyl groups.

In order to appreciate the polymeric nature of the structure of the compound, it is worthwhile to contrast the product with a simple product which results from the condensation of a silane having only a single silanol group in the amino silane. The reaction of;

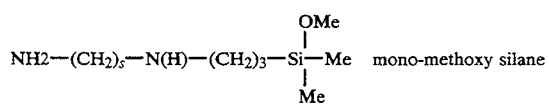

mono-methoxy silane with

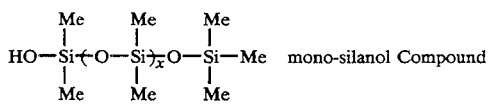

mono-silanol Compound produces :

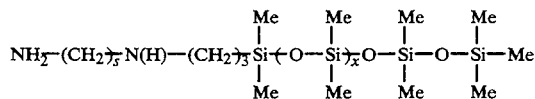

Me is methyl;
x is an integer from 10 to 2000;
s is an integer ranging from 1 to 3.

This compound lacks (a) durability due to the lack of an alkoxy or silanol group, (b) water solubility or dispersability due to the lack of an alkylene oxide present in the molecule, and (c) substantivity due to the lack of a three dimensional structure.

As will become clear when a difunctional silanol is reacted with a tri methoxy functional amino silane, a highly branched compound results. The branching from a tri functional alkoxy silane will be much greater than that experienced with a difunctional alkoxy silane. The product of the trifunctional alkoxy silane is more resinous and this is highly desirable when one intends to form a flexible durable film on textile substrates.

The compound of the present invention requires that the ratio of silanol hydroxyl equivalents to silane alkoxy group be less than 1:1. This will result in residual alkoxy groups which will lead to durability. The functional ratio of silanol groups to alkoxy group ranges from 1 silanol to 2-3 alkoxy.

The preferred reactants therefore are;

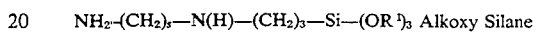
NH₂—(CH₂)ₛ—N(H)—(CH₂)₃—Si—(OR¹)₃  Alkoxy Silane

R¹ is methyl or ethyl;
s is an integer ranging from 1 to 3.
and

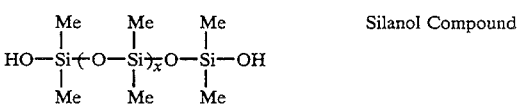

Silanol Compound x is an integer from 10 to 2000;
Me is methyl.

The resulting polymer network in it's most simple form resembles the following;

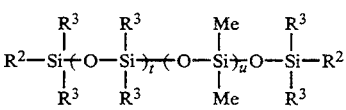

wherein;
Me is methyl;
R² is —(CH₂)₃—N(H)—((CH₂)ₛ—NH)ₖ—H
R³ is selected from the group consisting of —OMe and OH;
s is an integer ranging from 1 to 3
t is an integer ranging from 10 to 2,000;
u is an integer ranging from 0 to 2,000:
k is an integer from 0 to 3.

Since the free silanol groups in R³ also react a complex three dimensional polymer develops. The polymer is surprisingly reproducible and is controlled by the ratio of silane alkoxy group to silanol group. The useful ratio as stated is 1 silanol group to 2-3 alkoxy groups, with the preferred ratio of 1: 2.5.

The compounds clearly are high molecular weight products which are very richly functionalized. The high concentration of amino functionality makes them of interest as softeners, the high concentration of silanol group and residual alkoxy group makes them candidates for durability. Unfortunately, despite the needed three dimensional structure these materials are very oily and cannot be applied to fibers. They lack the desired water solubility or dispersability.

Reaction Sequence 2

Condensation with Dimethicone Copolyols

The compounds so prepared are reacted with dimethicone copolyols to produce a new polymer which has the needed alkylene oxide for solubility and can be applied to fibers from water. The three dimensional stability, the amino softener, the durability attributed to the silanol and alkoxy group as well as the water dispersability or solubility are now achieved.

Dimethicone copolyols are known. They conform to the following structures:

Terminal Dimethicone Copolyols

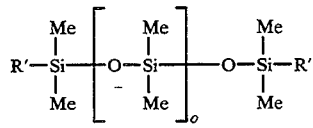

wherein;
Me is methyl;
R' is —(CH$_2$)$_3$—O—(EO)$_a$—(PO)$_b$—(EO)$_c$—H
o is an integer ranging from 1 to 100;
EO is —(CH$_2$CH$_2$—O)—;
PO is —(CH$_2$CH(CH$_3$)—O)—;
a, b and c are integers independently ranging from 0 to 20.

Comb Dimethicone Copolyols

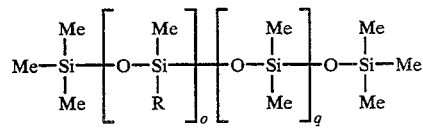

wherein;
Me is methyl;
o is an integer ranging from 1 to 100;
q is an integer ranging from 0 to 500;
R is —(CH$_2$)$_3$—O—(EO)$_a$—(PO)$_b$—(EO)$_c$—H
EO is —(CH$_2$CH$_2$—O)—;
PO is —(CH$_2$CH(CH$_3$)—O)—;
a, b and c are integers independently ranging from 0 to 20.

The insertion reaction results in the placing of the dimethicone copolyol compound within the above mentioned highly branched silicone compound. The dimethicone copolyol is added at a weight percent of between 98% and 50%. If the concentration exceeds 98% the durability is lost. If it is less than 50% the water solubility is lost.

The branching pattern, the substitution with (a) an amino group, (b) an alkylene oxide containing portion, (c) a reactive group selected from the group consisting of silanol hydroxyl and optionally a alkoxy group allows for a product which is durable when applied to fiber and hair.

The compounds are amino silicone polymer made by the reaction of an amino trialkoxy silane and a silanol to make an intermediate which is subsequently reacted with a dimethicone copolyol in the presence of alkaline catalyst.

In a preferred embodiment said trialkoxy silane conforms to the following structure;

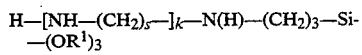

where in;

k is an integer ranging from 0 to 3;
s is an integer ranging from 1 to 3;
R1 is selected from the group consisting of methyl and ethyl.

In a preferred embodiment said silanol conforms to the following structure;

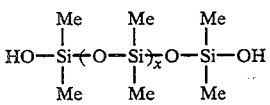

Me is methyl;
x is an integer from 10 to 2000.

In a preferred embodiment the dimethicone copolyol is selected from the group consisting of;
(a) Terminal dimethicone copolyol conforming to the following structure;

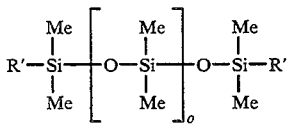

wherein;
Me is methyl;
R' is —(CH$_2$)$_3$—O—(EO)$_a$—(PO)$_b$—(EO)$_c$—H
EO is —(CH$_2$CH$_2$—O)—;
PO is —(CH$_2$CH(CH$_3$)—O)—;
a, b and c are integers independently ranging from 0 to 20;
o is an integer ranging from 1 to 100, and
(b) comb dimethicone copolyol conforming to the following structure;

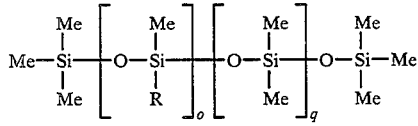

wherein;
Me is methyl;
R is —(CH$_2$)$_3$—O—(EO)$_a$—(PO)$_b$—(EO)$_c$—H
EO is —(CH$_2$CH$_2$—O)—;
PO is —(CH$_2$CH(CH$_3$)—O)—;
a, b and c are integers independently ranging from 0 to 20;
o is an integer ranging from 1 to 100;
q is an integer ranging from 0 to 500.

In a preferred embodiment the alkaline catalyst is selected from the group consisting of KOH and NaOH.
In still another preferred embodiment R1 is methyl.
In another preferred embodiment R1 is ethyl.
In another preferred embodiment k is 0.
In another preferred embodiment k is 1.
In another preferred embodiment k is 2.
In a preferred embodiment a is 2.
In another preferred embodiment a is 3.
In a preferred embodiment o is an integer from 10 to 50.
In a preferred embodiment the dimethicone copolyol is a terminal dimethicone copolyol conforming to the following structure;

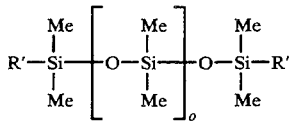

wherein;
Me is methyl;
R' is —(CH$_2$)$_3$—O—(EO)$_a$—(PO)$_b$—(EO)$_c$—H
EO is —(CH$_2$CH$_2$—O)—;
PO is —(CH$_2$CH(CH$_3$)—O)—;
a, b and c are integers independently ranging from 0 to 20;
o is an integer ranging from 1 to 100.

In another preferred embodiment the dimethicone copolyol is a comb dimethicone copolyol conforming to the following structure;

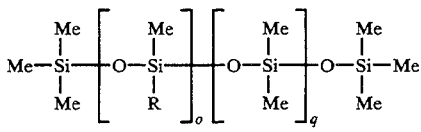

wherein;
Me is methyl;
R is —(CH$_2$)$_3$—O—(EO)$_a$—(PO)$_b$—(EO)$_c$—H
EO is —(CH$_2$CH$_2$—O)—;
PO is —(CH$_2$CH(CH$_3$)—O)—;
a, b and c are integers independently ranging from 0 to 20;
o is an integer ranging from 1 to 100;
q is an integer ranging from 0 to 500.

In a preferred embodiment the amount of dimethicone copolyol ranges from 50% by weight to 99% by weight.

RAW MATERIAL EXAMPLES (A) Silanol Compounds

Silanol compounds are well known and are marketed in the trade under many names. The compounds conform to the following generic structure;

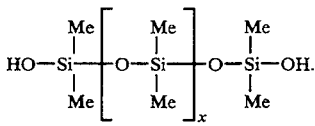

Compounds of the following structure are available from Siltech Inc. Norcross, Ga. and are marketed under the Siltech S series tradename shown;

| Example | Name | Molecular Weight | x |
|---|---|---|---|
| 1 | Siltech S 701 | 1,000 | 11 |
| 2 | Siltech S 706 | 6,000 | 80 |
| 3 | Siltech S 710 | 10,000 | 133 |
| 4 | Siltech S 750 | 50,000 | 673 |
| 5 | Siltech S 790 | 86,000 | 1160 |

(B) Amino Silane

Amino silane compounds are available from many manufacturers including Union Carbide, whom market under the tradename shown below.

| Example | Name | Structure |
|---|---|---|
| 6 | A-1100 | NH$_2$—(CH$_2$)$_3$—Si—(O—CH$_2$—CH$_3$)$_3$ |
| 7 | A-1110 | NH$_2$—(CH$_2$)$_3$—Si—(O—CH$_3$)$_3$ |
| 8 | A-1120 | NH—(CH$_2$)$_3$—Si—(O—CH$_3$)$_3$<br>\|<br>(CH$_2$)$_2$—NH$_2$ |
| 9 | A-1130 | NH—(CH$_2$)$_3$—Si—(O—CH$_3$)$_3$<br>\|<br>(CH$_2$)$_2$—NH—(CH$_2$)$_2$—NH$_2$ |
| 10 | — | NH—(CH$_2$)$_3$—Si—(O—CH$_2$—CH$_3$)$_3$<br>\|<br>(CH$_2$)$_2$—NH—(CH$_2$)$_2$—NH$_2$ |

(C) Dimethicone Copolyols

Many manufacturers offer a series of hydroxy silicone compounds suitable for use as raw materials in the preparation of the esters of the present invention. These materials are marketed under the many trade names. Siltech Inc, Union Carbide, Dow Corning, Mazer and many other manufacturers also offer the compounds commercially.

The preferred method of placing this type of reactive hydroxyl group into the silicone polymer is by the reaction of silanic hydrogen containing polymer with allyl alcohol alkoxylates. This technology is well known to those skilled in the art and are described in U.S. Pat. No. 4,083,856.

Additionally, hydroxy silicone compounds are available from Siltech Inc. Norcross, Ga. These compounds conform to the following generic structure;

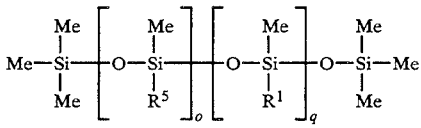

wherein;
Me is methyl;
R$^5$ is —(CH$_2$)$_3$—O—(EO)$_a$—(PO)$_b$(EO)$_c$—H
R$^1$ is selected from lower alkyl CH$_3$(CH)$_n$—or phenyl;
n is an integer from 0 to 8;
a, b and c are integers independently ranging from 0 to 20;
EO is an ethylene oxide residue —(CH$_2$CH$_2$—O)—;
PO is a propylene oxide residue —(CH$_2$CH(CH$_3$)—O)—;
o is an integer ranging from 1 to 100;
q is an integer ranging from 0 to 500.

| Example | Name | a | b | c | o | q |
|---|---|---|---|---|---|---|
| 11 | Siltech H 1000 | 3 | 0 | 0 | 2 | 54 |
| 12 | Siltech H 1100 | 10 | 5 | 10 | 10 | 100 |
| 13 | Siltech H 1200 | 20 | 20 | 20 | 2 | 56 |
| 14 | Siltech H 1300 | 10 | 10 | 10 | 6 | 26 |
| 15 | Siltech H 1400 | 0 | 10 | 0 | 4 | 200 |
| 16 | Siltech H 1500 | 5 | 5 | 5 | 2 | 50 |
| 17 | Siltech H 1600 | 0 | 6 | 0 | 10 | 25 |
| 18 | Siltech H 1700 | 0 | 0 | 0 | 5 | 10 |

Terminal Substituted Dimethicone Copolyol Compounds

Terminal substituted dimethicone copolyol compounds are well known and are marketed in the trade under many names.

The preferred method of placing this type of reactive hydroxyl group into the silicone polymer is by the reaction of terminal silanic hydrogen containing polymer with allyl alcohol alkoxylates. This technology is well known to those skilled in the art and are described in U.S. Pat. No. 4,083,856.

These materials are available from Siltech Inc. Norcross, Ga. and are marketed under the Siltech T series trade name.

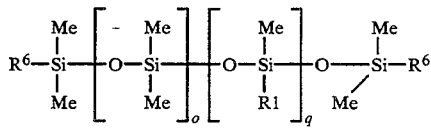

wherein;

Me is methyl;

$R^6$ is —$(CH_2)_3$—O—$(EO)_a$—$(PO)_b$—$(EO)_c$—H $R^1$ is selected from lower alkyl $CH_3$ $(CH)_n$—or phenyl;

n is an integer from 0 to 8;

a, b and c are integers independently ranging from 0 to 20;

EO is an ethylene oxide residue —$(CH_2CH_2$—O)—;

PO is a propylene oxide residue —$(CH_2CH(CH_3)$—O)—;

o is an integer ranging from 1 to 100;

q is an integer ranging from 0 to 500.

| Example | Name | a | b | c | Equivalent Molecular Weight |
|---|---|---|---|---|---|
| 19 | Siltech T 701 | 0 | 0 | 0 | 1,000 |
| 20 | Siltech T 706 | 5 | 1 | 0 | 6,000 |
| 21 | Siltech T 710 | 2 | 1 | 1 | 10,000 |
| 22 | Siltech T 750 | 10 | 5 | 10 | 50,000 |
| 23 | Siltech T 790 | 20 | 20 | 20 | 86,000 |

EXAMPLES (Reaction Sequence #1)

General Conditions

The reaction is conducted using the following general procedure;

To a suitable reaction vessel equipped with mechanical agitation, thermometer, and dean stark trap is added the specified amount of the specified silanol. The agitation is started. Next the specified amount of water is added, followed by the specified amount of the specified silane. The reaction mass is heated to 80–85 C. The reaction mass is held at this temperature for 3–5 hours. During that time the reaction mass becomes clear and homogeneous. The product is converted into the final product as shown below.

Solvents like ethanol, methanol or other solvents can be added to lower the viscosity if desired.

| Example | Silanol Example | Silanol Grams | Silane Example | Silane Grams | Water Grams |
|---|---|---|---|---|---|
| 24 | 1 | 500.0 | 6 | 221.4 | 54.0 |
| 25 | 2 | 3000.0 | 7 | 179.3 | 54.0 |
| 26 | 3 | 5000.0 | 8 | 222.4 | 54.0 |
| 27 | 4 | 25000.0 | 9 | 265.5 | 54.0 |
| 28 | 5 | 43000.0 | 10 | 309.5 | 54.0 |
| 29 | 5 | 43000.0 | 6 | 221.4 | 54.0 |
| 30 | 4 | 25000.0 | 7 | 179.3 | 54.0 |
| 31 | 3 | 5000.0 | 8 | 222.4 | 54.0 |
| 32 | 2 | 3000.0 | 9 | 265.5 | 54.0 |
| 33 | 1 | 500.0 | 10 | 309.5 | 54.0 |

Examples (Reaction Sequence #2)

General Conditions

The reaction is conducted using the following general procedure;

To a suitable reaction vessel containing the intermediate prepared above (examples 24–33) is added the specified amount of dimethicone copolyol and 0.1% KOH, The reaction mass is heated to 175–195 C. and held for 1–5 hours. During this time the reaction mass becomes clear and homogeneous.

| Example | Sequence 1 Reaction Product Example | Dimethicone Copolyol Example | Dimethicone Copolyol Grams |
|---|---|---|---|
| 34 | 24 | 11 | 775.4 |
| 35 | 25 | 12 | 4849.9 |
| 36 | 26 | 13 | 70100.7 |
| 37 | 27 | 14 | 75958.5 |
| 38 | 28 | 15 | 245726.5 |
| 39 | 29 | 16 | 100975.9 |
| 40 | 30 | 17 | 290182.9 |
| 41 | 31 | 18 | 6449.0 |
| 42 | 32 | 19 | 29875.5 |
| 43 | 33 | 20 | 1603.6 |
| 44 | 24 | 21 | 3101.6 |
| 45 | 25 | 22 | 378182.9 |
| 46 | 26 | 23 | 15829.2 |
| 47 | 27 | 11 | 47021.9 |
| 48 | 28 | 12 | 65042.3 |
| 49 | 29 | 13 | 245227.3 |
| 50 | 30 | 14 | 479432.7 |
| 51 | 31 | 15 | 70100.7 |
| 52 | 32 | 16 | 29875.5 |
| 53 | 33 | 17 | 1055.4 |

Applications Examples

Control

The following compound was prepared by the reaction of Dow Corning CSF and amino Silicone compound having no free silanol or alkoxy groups with Siltech H-1000. The following compound resulted;

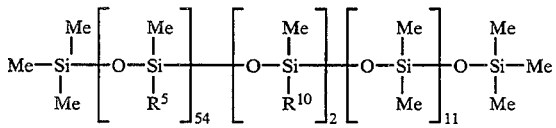

wherein;

Me is methyl;

$R^5$ is —$(CH_2)_3$—O—$(EO)_3$—$(PO)_0$—$(EO)_0$—H

EO is an ethylene oxide residue —$(CH_2CH_2$—O)—;

PO is a propylene oxide residue —$(CH_2CH(CH_3)$—O)—.

Compounds of the Present Invention

This compound was compared to Example 34 of the present invention which has substantially the same values for each of the variables given above, however the material is highly branched and containing free hydroxy and alkoxy groups present.

Both materials were applied to polyester fabric at 1% concentration. Both materials gave a soft hand as applied, however after two washings the control compound lost it's softness, while the compound of the present invention retained it's softness for over fifteen washings. This is because the compound of the present invention (a) has branching, the control did not, and (b) the compound of the present invention has silanol and or alkoxy groups present to attach to the substrate, while the control did not.

We have found that the materials prepared in accordance with the present invention are durable, water soluble or dispersible and non-yellowing. The durability is due to the presence of the silanol groups on the silicone which was originally in the silane. Amino products which do not have the silanol groups do not exhibit durability.

The products of the present invention can be placed into aqueous systems without emulsifiers. This is a tremendous advantage to the formulator, since emulsions of typical amino silicones have a tendency to split with time, extremes of temperature or agitation. When the emulsions of standard amino silicones split, the oil is deposited on the textile or fiber substrate and interfere with dying causing what is called in the market "fish eyes". The products of the present invention do not do this.

What is claimed:

1. An amino silicone polymer made by the reaction or an amino trialkoxy silane conforming to the following structure:

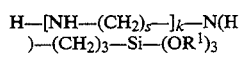

wherein;
R$^1$ is methyl or ethyl;
k is an integer ranging from 0 to 3;
s is an integer ranging from 1 to 3;
with and a silanol, conforming to the following structure:

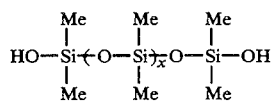

wherein;
x is an integer from 10 to 2000;
Me is methyl;
to make an intermediate which is subsequently reacted with a dimethicone copolyol conforming to one of the following structures:

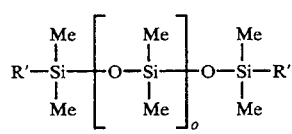

wherein;
Me is methyl;
R' is —(CH$_2$)$_3$—O—(EO)$_a$—(PO)$_b$—(EO)$_c$—H
o is an integer ranging from 1 to 100;
EO is —(CH$_2$CH$_2$—O)—;
PO is a —(CH$_2$CH(CH$_3$)—O)—;
a, b and c are integers independently ranging from 0 to 20;
or

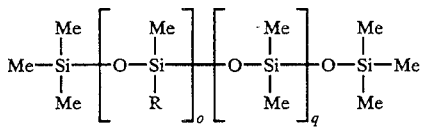

wherein;
Me is methyl;
o is an integer ranging from 1 to 100;
q is an integer ranging from 0 to 500;
R is —(CH$_2$)$_3$—O—(EO)$_a$—(PO)$_b$—(EO)$_c$—H
EO is —(CH$_2$CH$_2$—O)—;
PO is a —(CH$_2$CH(CH$_3$)—O)—;
a, b and c are integers independently ranging from 0 to 20;
in the presence of alkaline catalyst.

2. A compound of claim 1 wherein said trialkoxy silane conforms to the following structure;

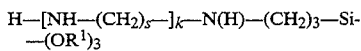

wherein;
k is 0;
s is an integer ranging from 1 to 3;
R1 is selected from the group consisting of methyl and ethyl.

3. A compound of claim 1 wherein said trialkoxy silane conforms to the following structure;

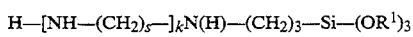

wherein;
k is 2;
s is an integer ranging from 1 to 3;
R1 is selected from the group consisting of methyl and ethyl.

4. A compound of claim 1 wherein said dimethicone copolyol conforms to the following structure;

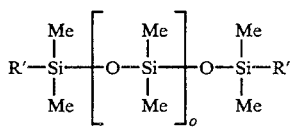

wherein;
Me is methyl;
R' is —(CH$_2$)$_3$—O—(EO)$_a$—(PO)$_b$—(EO)$_c$—H;
EO is —(CH$_2$CH$_2$—O)—;
PO is a —(CH$_2$CH(CH$_3$)—O)—
a, b and c are integers independently ranging from 0 to 20;
o is an integer ranging from 1 to 100.

5. A compound of claim 1 wherein said dimethicone copolyol conforms to the following structure;

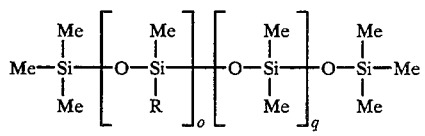

wherein;
Me is methyl;
R is —(CH$_2$)$_3$—O—(EO)$_a$—(PO)$_b$—(EO)$_c$—H;
EO is —(CH$_2$CH$_2$—O)—;
PO is a —(CH$_2$CH(CH$_3$)—O)—
a, b and c are integers independently ranging from 0 to 20;

o is an integer ranging from 1 to 100;
q is an integer ranging from 0 to 500.

6. A compound of claim 1 wherein R1 is methyl.
7. A compound of claim 1 wherein R1 is ethyl.
8. A compound of claim 1 wherein k is 0.
9. A compound of claim 1 wherein k is 1.
10. A compound of claim 1 wherein k is 2.
11. A compound of claim 1 wherein s is 2.
12. A compound of claim 1 wherein s is 3.
13. A compound of claim 2 wherein o is an integer from 0 to 50.
14. A compound of claim 1 wherein said alkaline catalyst is selected from the group consisting of KOH and NaOH.

* * * * *